United States Patent
Liu et al.

(10) Patent No.: US 10,973,688 B2
(45) Date of Patent: Apr. 13, 2021

(54) EYE SUCTION LOSS AND CORNEAL APPLANATION DETECTION IN OPHTHALMIC DOCKING SYSTEM USING OPTICAL SIGNAL

(71) Applicant: AMO Development, LLC, Santa Ana, CA (US)

(72) Inventors: Harvey I. Liu, Fremont, CA (US); Mohammad Saidur Rahaman, Santa Clara, CA (US); Hong Fu, Pleasanton, CA (US); Griffith E. Altmann, Ladera Ranch, CA (US)

(73) Assignee: AMO Development, LLC, Santa Ana, CA (US)

( * ) Notice: Subject to any disclaimer, the term of this patent is extended or adjusted under 35 U.S.C. 154(b) by 209 days.

(21) Appl. No.: 16/355,662

(22) Filed: Mar. 15, 2019

(65) Prior Publication Data

US 2020/0289318 A1 Sep. 17, 2020

(51) Int. Cl.
A61F 9/009 (2006.01)
A61F 9/008 (2006.01)

(52) U.S. Cl.
CPC .......... *A61F 9/009* (2013.01); *A61F 9/00827* (2013.01); *A61F 9/00834* (2013.01); *A61F 9/00836* (2013.01); *A61F 2009/00844* (2013.01); *A61F 2009/00855* (2013.01);
(Continued)

(58) Field of Classification Search
CPC ............ A61F 9/009; A61F 2009/00844; A61F 9/00827
See application file for complete search history.

(56) References Cited

U.S. PATENT DOCUMENTS

| 7,390,089 B2 | 6/2008 | Loesel et al. |
| 9,296,069 B2 | 3/2016 | Bischoff et al. |
| 9,398,979 B2 | 7/2016 | Hohla et al. |

(Continued)

FOREIGN PATENT DOCUMENTS

WO 2015119892 A1 8/2015

OTHER PUBLICATIONS

Co-pending U.S. Appl. No. 16/112,507, filed Aug. 24, 2018.
International Search Report for Application No. PCT/IB2020/052215, dated Jun. 18, 2020, 2 pages.

*Primary Examiner* — Ahmed M Farah
*Assistant Examiner* — Zahed Kabir
(74) *Attorney, Agent, or Firm* — Johnson & Johnson Surgical Vision, Inc.

(57) ABSTRACT

An ophthalmic laser surgical system uses a confocal detector assembly to continuously detect a confocal signal during laser treatment, and based on the confocal signal, detects in real time a loss of tissue contact with the patient interface (PI) output surface. The detection is partly based on the change of reflectivity at the PI output surface when the optical interface changes from a lens-tissue interface to a lens-air interface. The behavior of the confocal signal upon loss of tissue contact is dependent on the treatment laser scan pattern being performed at the time of tissue contact loss. Thus, different confocal signal analysis algorithms are applied to detect tissue contact loss during different scans, such as the bed cut and side cut for a corneal flap. The real time confocal signal may also be used during eye docking to detect the establishment of tissue contact with the PI output surface.

20 Claims, 6 Drawing Sheets

(52) U.S. Cl.
CPC ............... *A61F 2009/00872* (2013.01); *A61F 2009/00897* (2013.01)

(56) References Cited

U.S. PATENT DOCUMENTS

| | | | |
|---|---|---|---|
| 9,504,609 B2 | 11/2016 | Kurtz | |
| 9,549,670 B2 | 1/2017 | Gonzalez et al. | |
| 2004/0070761 A1 | 4/2004 | Horvath et al. | |
| 2005/0192562 A1 | 9/2005 | Loesel et al. | |
| 2008/0078752 A1 | 4/2008 | Bischoff et al. | |
| 2009/0118717 A1* | 5/2009 | Brownell | A61F 9/009 606/4 |
| 2014/0128731 A1* | 5/2014 | Gonzalez | A61B 3/107 600/427 |
| 2014/0155873 A1 | 6/2014 | Bor | |
| 2015/0272782 A1 | 10/2015 | Schuele et al. | |
| 2016/0089270 A1 | 3/2016 | Fu | |
| 2016/0250068 A1* | 9/2016 | Dewey | A61F 9/00754 606/4 |
| 2016/0303684 A1 | 10/2016 | Bischoff et al. | |
| 2016/0354246 A1* | 12/2016 | Gooding | A61B 90/39 |
| 2017/0011501 A1* | 1/2017 | Gonzalez | G06T 7/70 |
| 2018/0116870 A1 | 5/2018 | Garcia et al. | |

\* cited by examiner

EYE SUCTION LOSS AND CORNEAL APPLANATION DETECTION IN OPHTHALMIC DOCKING SYSTEM USING OPTICAL SIGNAL

BACKGROUND OF THE INVENTION

Field of the Invention

This invention relates to an ophthalmic laser system and method, and in particular, it relates to an ophthalmic laser system employing a confocal optical system and related method for detecting the contact and loss of contact between the eye's surface and the patient interface lens of the laser system throughout all phases of the procedure workflow.

Description of Related Art

An ophthalmic laser system, such as one used to modify the cornea of the eye to achieve refractive correction, generally includes a laser device that generates a laser beam, such as a pulsed laser beam, and a beam delivery optical system that delivers a focused spot of the laser beam into a patient's eye. The beam delivery system includes a scanner sub-system for scanning the laser beam focus in three dimensions according to a scan pattern within a desired volume of the eye to effectuate various desired treatments, such as tissue incisions. An example of a laser system is described in detail in U.S. Pat. Appl. Pub. No. 2016/0089270, published Mar. 31, 2016, entitled Systems and Methods for Lenticular Laser Incision, the disclosure of which is herein incorporated by reference in its entirety.

In such systems, during the refractive surgical procedure, the patient's eye is physically coupled to the laser beam delivery system via a disposable patent interface (PI) device, which is physically attached at its proximal end to a housing of the beam delivery system and at its distal end to the surface of the eye. In some systems, the distal end of the PI device includes an optical lens designed to contact the corneal of the eye, and a suction ring having a flexible skirt configured to forming a suction channel with the eye surface. Prior to commencing laser treatment of the eye, the eye is docked to the PI device, such that the PI lens contacts the cornea, and the flexible skirt contacts the surface of the eye (e.g. the sclera) to form an enclosed suction channel. A suction force is applied to the suction channel by an external vacuum source to securely couple the eye to the PI device. An example of a PI device is described in U.S. Pat. Appl. Pub. No. 2018/0116870, published May 3, 2018, entitled Patient Interface Device for Ophthalmic Surgical Laser System, the disclosure of which is herein incorporated by reference in its entirety.

Secured eye suction during laser refractive surgery to prevent eye movement and ensure consistent optical contact integrity is critical for safety control of the procedure. This is because the calibration of the laser beam focus position (i.e. the treatment position) is relative to the PI device, such as the distal surface of the PI lens. When suction is lost either locally or globally, eye movement and loss of tissue contact with the PI lens can lead to ineffective surgical cut or surgical cut at unintended positions and result in permanent injury to the eye. Therefore, a fast suction loss and cornea contact loss detection system is important, so that when such a safety critical anomaly is detected, the laser surgical treatment can be immediately paused or terminated. It is also desirable for such a detection system to have different severity levels and regional identifications of the suction loss so that appropriate recovery actions can be taken by the surgeon.

In addition, in refractive cornea surgery, during the eye docking process (a process by which the eye is brought into contact with and secured to the PI device), it is an important goal to achieve the desired cornea applanation with full adequate contact between the tissue and the PI lens. A robust applanation detection for adequate tissue contact is desirable for providing feedback to surgeons for successful docking prior to executing laser surgery.

There are also treatment anomalies due to inadequate full eye contact that a fast detection system could be useful in preventing complications. These include phenomenon such as pseudo suction and excess interface bubble formation. In pseudo suction, the vacuum suction is still active with no indication of vacuum loss, but the conjunctiva closes the suction port instead of the eye. This would result in eye movement and poor eye applanation without indication of vacuum loss. Another anomaly that would benefit from a fast optical detection is excess local bubble formation at the PI lens interface. In this case, the bubbles generated from the laser tissue interaction migrate to the lens interface and potentially block the subsequent treatment due to scattering.

Currently known eye docking systems primarily utilize vacuum sensors placed at different points along the suction control loop to detect suction loss anomaly. The main drawback of this type of direct vacuum sensing is that it is a single dimensional average vacuum level signal without local information. This tends to be less sensitive and is only useful for global suction loss detection in most severe conditions.

There are also imaging systems that image the eye for detecting movement of the eye under suction. This is often used as an add-on to the direct vacuum sensing system. However, due to the complexity of the image recognition algorithms and also the wide distributions of eye patterns and docking conditions, the detection is often not robust and prone to false positives.

SUMMARY

Accordingly, the present invention is directed to an ophthalmic laser surgical system and related method that substantially obviate one or more of the problems due to limitations and disadvantages of the related art.

An object of the present invention is to provide confocal signal-based real time monitoring of loss of tissue contact with the PI.

Additional features and advantages of the invention will be set forth in the descriptions that follow and in part will be apparent from the description, or may be learned by practice of the invention. The objectives and other advantages of the invention will be realized and attained by the structure particularly pointed out in the written description and claims thereof as well as the appended drawings.

To achieve the above objects, the present invention provides an ophthalmic laser surgical method for treating an eye of a patient, which includes: coupling the eye to a patient interface device, including forming a direct contact of an output surface of the patient interface device with an eye tissue of the eye; a laser system generating a laser beam and focusing it to a laser beam focus; scanning devices of the laser system, controlled by a controller, scanning the laser beam focus within the eye according to one or more scan patterns; while the laser beam focus is being scanned within the eye, a confocal assembly of the laser system continuously detecting a confocal signal, the confocal signal representing an intensity of a portion of the laser beam that has been reflected by the eye, focused by one or more lenses onto a pinhole, passed through the pinhole, and detected by a photodetector behind the pinhole; based on the confocal signal, the controller detecting, in real time, a loss of the direct contact between the output surface of the patient interface device and the eye tissue; and in response to detecting the loss of the direct contact, the controller performing a predefined corrective action.

In another aspect, the present invention provides a method for docking an eye of a patient to a laser system, which includes: coupling a patient interface device to a housing of the laser system; the laser system generating a laser beam having an eye safe energy level and focusing it to a laser beam focus located at an output surface of the patient interface device; while the laser beam focus is being focused at the output surface of the patient interface device, a confocal assembly of the laser system continuously detecting a confocal signal, the confocal signal representing an intensity of a portion of the laser beam that has been reflected by the output surface, focused by one or more lenses onto a pinhole, passed through the pinhole, and detected by a photodetector behind the pinhole; a controller continuously monitoring the confocal signal; while the confocal signal is being continuously generated and monitored, moving the patient interface device and the patient's eye toward each other; based on the confocal signal, the controller detecting, in real time, formation of a direct contact between the output surface of the patient interface device and the eye; and in response to detecting the formation of the direct contact, the controller performing a predefined responsive action.

In another aspect, the present invention provides an ophthalmic laser surgical system, which includes: a patient interface device having an output surface, the patient interface device configured to be coupled to a patient's eye to form a direct contact of the output surface with an eye tissue of the eye; a laser device configured to generate a laser beam; a focusing lens configured to focus the laser beam to a laser beam focus; scanning devices configured to scan the laser beam focus; a confocal assembly, including a beam splitter configured to sample a reflected portion of the laser beam that has been reflected by the eye or the output surface of the patient interface or both, a pinhole, a lens configured to focus the sampled reflected laser beam to the pinhole, and a detector located behind the pinhole configured to detect an intensity of the laser beam that has passed through the pinhole as a confocal signal; a controller coupled to the scanning device and the confocal assembly, configured to: control the scanning devices to scan the laser beam focus according to one or more scan patterns; continuously receive the confocal signal generated by the confocal assembly; based on the confocal signal, detect, in real time, a change in a state of direct contact between the output surface of the patient interface device and the eye tissue, including a change from a presence of direct contact to an absence of a direct contact, and a change from an absence of a direct contact to a presence of a direct contact; and in response to detecting the change of the state of direct contact, perform a predefined responsive action.

In another aspect, the present invention provides a computer program product comprising a computer usable non-transitory medium (e.g. memory or storage device) having a computer readable program code embedded therein for controlling a data processing apparatus, the computer readable program code configured to cause the data processing apparatus to execute the above method.

It is to be understood that both the foregoing general description and the following detailed description are exemplary and explanatory and are intended to provide further explanation of the invention as claimed.

DETAILED DESCRIPTION OF PREFERRED EMBODIMENTS

Figure 1:
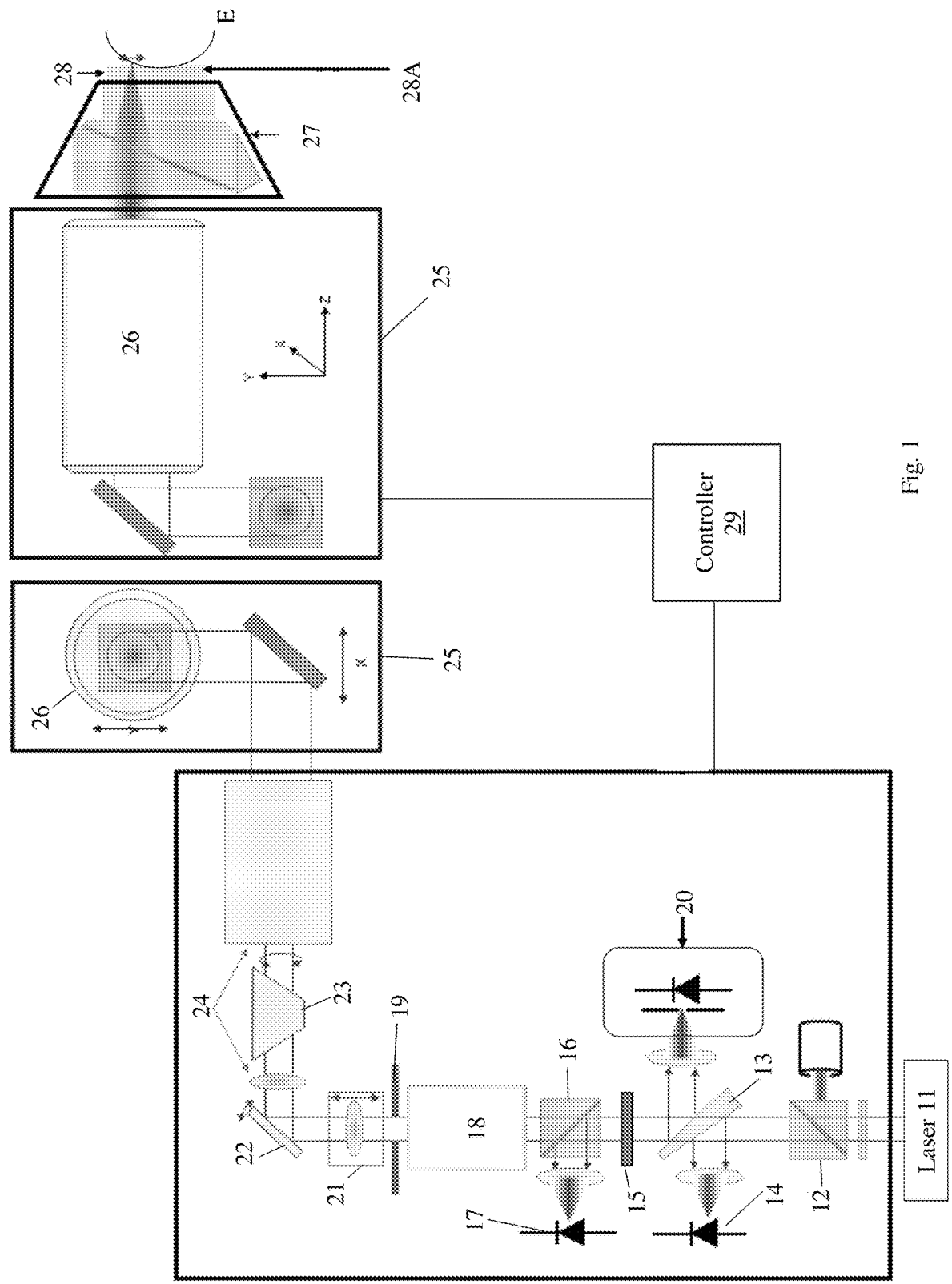
FIG. 1 schematically illustrates a surgical ophthalmic laser system in which a cornea contact detection method according to embodiments of the present invention may be implemented.

FIG. 1 schematically illustrates a surgical ophthalmic laser system in which a cornea contact detection method according to embodiments of the present invention may be implemented. Not all components shown in FIG. 1 are necessary. The laser system 10 includes a laser device 11 that generates a pulsed laser beam, an energy control component 12 that includes a polarization beam splitter and a beam dump, a beam splitter 13 that samples the laser beam for a power monitor 14, a shutter 15, a beam splitter 16 that samples the beam for a shutter monitor 17, a pre-beam expander 18, and a beam shaping aperture 19. These components function to generate a laser beam suitable for ophthalmic treatment. The system 10 also includes a confocal detection assembly 20 which will be described in more detail later.

The system 10 further includes a fast Z-scanner 21, a resonant scanner 22, a prism (scan line rotator) 23, a beam expander 24, movable X-Y stages 25 (FIG. 1 shows both a view along the Z axis and a view along the X axis), and an objective lens 26 for focusing the beam to a focus spot. The fast-Z scanner 21 utilizes a lens that can be scanned in the Z direction (the direction of the optical axis of the system), which will modify the depth (Z direction) of the laser beam focus in the eye tissue. The resonant scanner 22 scans the laser beam focus back and forth in a scan line (the fast scan line) in the X-Y direction (directions perpendicular to the Z direction) at high frequency, and the prism 23 rotates the direction of the fast scan line in the X-Y plane. The X-Y stages 25 move the laser beam focus (the location of the fast scan line) in the X-Y direction. The objective lens 26 is movable to move the laser beam focus in the Z direction at a slower speed than the fast-Z scanner 21. The fast Z-scanner 21, the resonant scanner 22, the X-Y stages 25 and the moveable objective lens 26 collectively achieve the movement and scanning of the laser beam focus within the eye tissue to perform modification of the tissue.

An additional optical component 27 is located downstream of the objective 26, for coupling to a disposable patient interface (PI) device. The optical component may include visualization optics (e.g. reflectors) to provide an optical signal to an imaging system (not shown) which can provide various monitoring and measurement functions. The disposable PI device has an output lens 28 with a distal surface (PI output surface) 28A which is transverse to the optical axis, configured to contact the eye surface during the ophthalmic procedure.

Various components of the laser system are coupled to a control sub-system 29 which employs a computer and/or processors and/or hardware circuitry, including a memory storing computer executable programs and a processor configured to execute the programs.

A laser system similar to that shown in FIG. 1, and in which embodiments of the present invention may be implemented, is described in detail in the above-referenced U.S. Pat. Appl. Pub. No. 2016/0089270. Other suitable laser system may also be used to implement the present invention.

Figure 2:
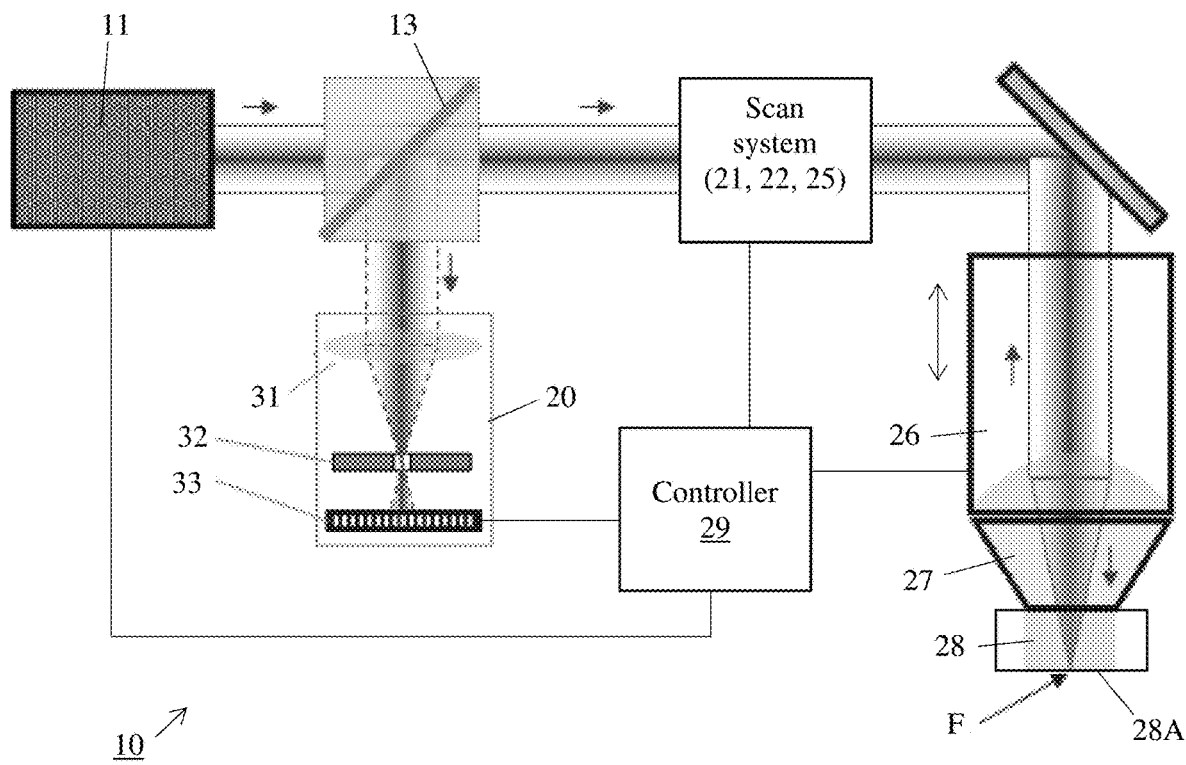
FIG. 2 schematically illustrates a portion of the surgical ophthalmic laser system of FIG. 1, showing details of the confocal detection system.

FIG. 2 schematically illustrates a portion of the ophthalmic laser system 10 of FIG. 1 that relates to the confocal system.

More generally, confocal microscopy is a widely used tool in biological imaging, because it significantly improves the contrast of images compared to wide field microscopy, and it allows depth segmenting. A confocal microscope is based on a double filtering operation: a certain volume inside the sample is selectively illuminated by a focused beam, and light originating from this focal volume is selectively observed using a pinhole in the detection pathway. The pinhole is located in a plane conjugated with the focal plane, and suppresses light originating from any location other than the focal volume. With this method, a point of a sample can be probed with higher contrast with respect to its surroundings. Images are built by scanning the probed focal volume inside the sample. In typical biological media, confocal microscopy allows one to obtain clear, background free images up to a certain depth.

As shown in FIG. 2, a part of the laser beam generated by the laser source 11 passes through the beam splitter 13, and after passing through other optical components including the scanning devices 21, 22, 25, is focused by the objective lens 26. The laser light that exits the objective lens 26 is partially reflected by the PI output surface 28A and/or the eye tissue, and the reflected laser light travels backwards into the objective lens. Note that in the example of FIG. 2, the laser beam focus F is located at the PI output surface 28A, but it can be located in the eye tissue below the PI output surface 28A. After the back-reflected laser light is focused by the objective lens 26 into a parallel beam and pass through the other optical components including the scanning devices, a part of the reflected laser light is reflected by the beam splitter 13 into the confocal detection assembly 20. The confocal detection assembly 20 includes a lens 31 (referred to as the confocal lens), a pinhole 32, and a light intensity detector 33 such as photodiodes. The confocal lens 31 is configured to focuses the parallel laser beam to the pinhole 32, and the light that passes through the pinhole is detected by the detector 33. Due to the presence of the pinhole, only light reflected by the volume of sample (e.g. eye tissue) located at the focal point of the laser beam will pass through the pinhole and contribute significantly to the detected confocal signal.

Figure 3:
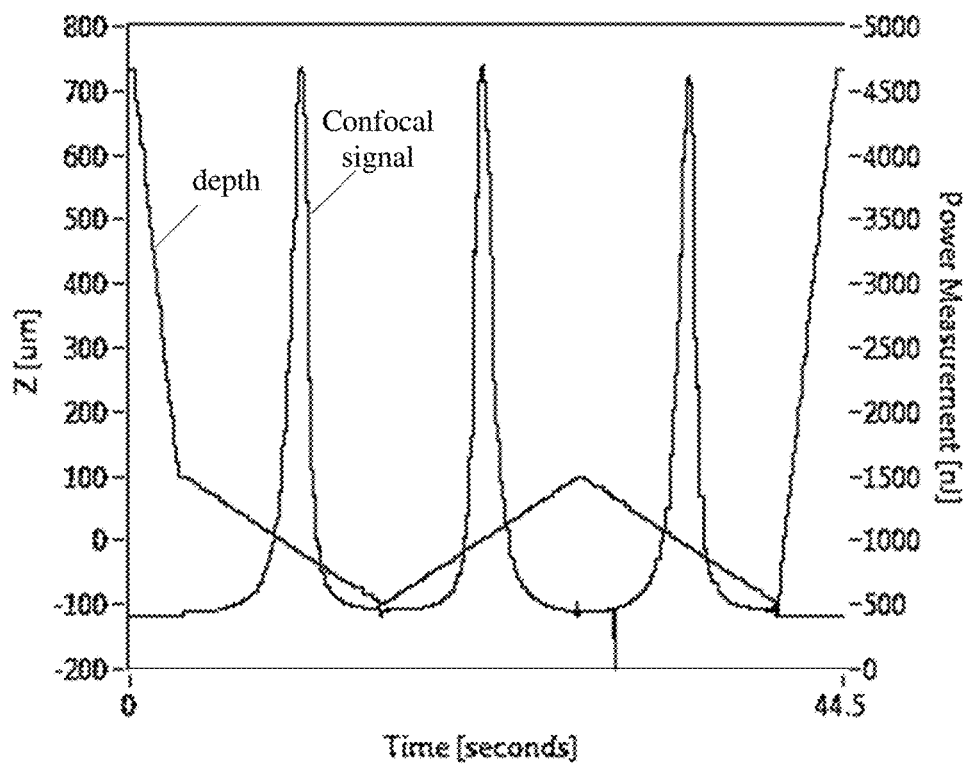
FIG. 3 illustrates an example of confocal signal peaks as the laser beam focus crosses the PI output surface.

The confocal optical system, which is integrated in the laser treatment path and uses the treatment laser as the source as described above, can be used to detect the PI output surface position, and to calibrate the objective lens setting so as to control the Z position of the laser beam focus relative to the PI output surface. The change in refractive index across the PI output surface causes the surface to reflect light, which will produce a peak signal at the confocal sensor 33 when the depth of the laser beam focus is moved and crosses the PI output surface. An example is shown in FIG. 3, where three sharp peaks in the confocal signal is seen when the laser beam focus position crosses Z=0, from either direction. Such a confocal signal can be used to calibrate the Z (depth) position of the PI output surface and set the precise treatment depth relative to that Z position. The Z position calibration is performed by placing a reference reflective surface (e.g. the PI output surface) at a defined position in front of the objective 26 (e.g. when the PI is physically coupled to the laser system housing), and scanning the laser beam focus in the Z direction using the objective 26, while recording the signal detected by the confocal detector 33. The setting of the objective 26 that corresponds to the peaks in the confocal signal can then be used to calibrate the settings of the objective 26. Examples of Z position calibration methods are described in co-pending U.S. patent application Ser. No. 16/112,507, filed Aug. 24, 2018, entitled Detection of Optical Surface of Patient Interface for Ophthalmic Laser Applications Using a Non-Confocal Configuration. Typically, such Z position calibration is performed prior to coupling the patient's eye to the PI.

Embodiments of the present invention provide a method that uses the confocal optical system 20 to detect and evaluate the integrity of the eye coupling to the PI during laser treatment and also to provide feedback for cornea applanation during the docking process. This method is performed by continuously detecting and monitoring the confocal signal throughout the laser treatment process, and analyzing the confocal signal in real time as the treatment is being performed. Because the confocal signal is sensitive and ultra-fast (approximately 1 kHz), the method provides sensitive, real-time monitoring of tissue contact loss.

The method of detecting tissue contact loss at the PI output surface is based on the recognition that the level of light reflection at the PI output surface is significantly different when the PI output surface is exposed to air as compared to when the PI output surface is in direct contact with eye tissue. The reflectivity of an optical interface between two optical media is dependent on the refractive index difference of the optical media involved. The PI lens material (glass), for example, has a typical refractive index of 1.4-1.5; the refractive index of the cornea is approximately 1.3, while that of air is 1.0. Thus, when the PI output surface is exposed to air, due to the relatively large change in refractive index at the glass-air interface, the laser beam from the objective lens experiences a relatively strong reflection at the PI output interface. On the other hand, when the PI output surface is in direct contact with eye tissue, the refractive index change at the glass-tissue interface is relatively small, and the laser beam from the objective lens experiences a relatively small reflection at the PI output interface.

How this difference of reflectivity at the PI output surface affects the confocal signal depends on the depth of the laser beam focus.

Figure 4A:
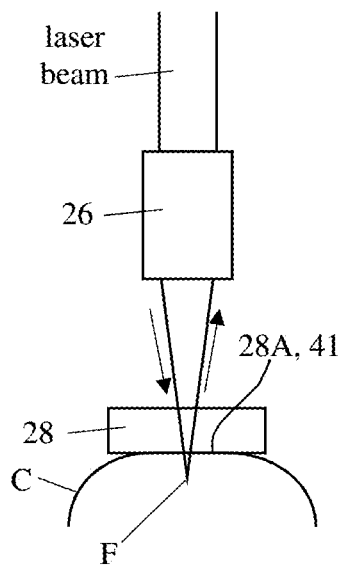
FIGS. 4A and 4B schematically illustrates a portion of the laser system when the PI lens is in contact with the cornea and when it is not in contact with the cornea, respectively.
Figure 4B:
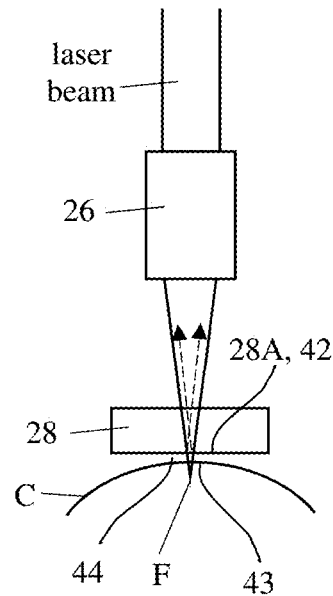

In a first example, schematically illustrated in FIGS. 4A and 4B, the PI output surface 28A is initially in direct contact with the cornea, and the laser beam is being scanned in a scan pattern where the laser beam focus is confined within an X-Y plane inside the cornea; at some time point during the scan, tissue contact with the PI lens is lost, but the laser beam focus is still within the cornea (i.e. the eye did not move too far away from the PI lens).

When the PI output surface 28A is in the normal conditions where it is in direct contact with the cornea C (FIG. 4A), an optical interface 41 is formed between the PI glass 28 and the cornea. On the other hand, when tissue contact is lost (FIG. 4B), a thin air gap 44 develops between the PI glass 28 and the cornea C, resulting in two optical interfaces: the first optical interface 42 between the PI glass 28 and air, and the second optical interface 43 between air and the cornea. The first optical interface 42, between the PI glass 28 and air, has a higher light reflectivity than the optical interface 41 between the PI glass and the cornea, due to the larger change of refractive index across the interface 42 as compared to interface 41. Moreover, the second optical interface 43 introduces additional light reflection.

The incoming laser light that is reflected away at the optical interface 42 (indicated by the dashed lines with arrows in FIG. 4B) appears to emanate from a point above the interface 42 which is a mirror image of the laser beam focus F with respect to the optical interface 42. Because the light reflected by interface 42 does not appear to emanate from the focus point F of the objective lens 26, it does not contribute to the confocal signal. Similarly, the incoming laser light that is reflected away at the second interface 43 does not contribute to the confocal signal. Moreover, the tissue surface 43 is typically non-planar since it is not in contact with the PI glass, so it scatters light in random directions which also reduces the overall signal detected by the confocal system. As a result, the intensity of the laser light reaching the focus point F is reduced when direct tissue contact with the PI glass 28 is lost. Moreover, the reflected light from the laser beam focus F in the tissue will also experience increased loss due to reflections at the two interfaces 42 and 43, which results in further reduce the confocal signal. Therefore, when tissue contact is lost, even though the laser beam focus remains inside the cornea and the reflective property of the cornea at the laser beam focus remains substantially unchanged, the detected confocal signal drops significantly.

Figure 5A:
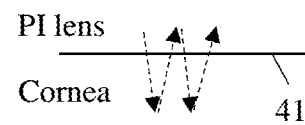
FIGS. 5A and 5B schematically illustrates the situation when the PI lens is in contact with the cornea and when it is not in contact with the cornea, respectively, during a laser scan where the laser beam focus periodically crosses the PI surface.
Figure 5B:
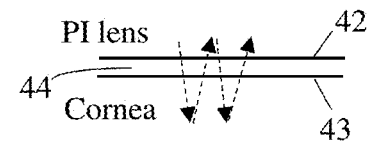

In a second example, schematically illustrated in FIGS. 5A and 5B, the PI output surface is initially in direct contact with the cornea and the laser beam is being scanned in a vertical scan pattern, where the laser beam focus is moved in the depth (Z) direction (as indicated by the dashed lines with arrows) back and forth and crosses the PI output surface periodically, while also moving in the X-Y directions. At some point during the scan, tissue contact with the PI lens is lost, but the laser beam focus continues to cross the PI output surface back and forth periodically. In this example, in the normal condition where the PI surface is in direct contact with the tissue (FIG. 5A), the confocal signal exhibits periodic sharp peaks when the laser beam focus crosses the optical interface 41 between the PI glass 28 and the cornea C, similar to the peaks shown in FIG. 3.

When tissue contact with the PI lens is lost (FIG. 5B), similar to the first example, a thin air gap 44 develops between the PI glass 28 and the cornea C, and two optical interfaces 42 and 43 are formed. The first optical interface 42, between the PI glass 28 and air, is located at the same depth as the optical interface 41 before tissue contact is lost, but has a higher reflectivity as described earlier. Therefore, when the laser beam focus is scanned in the Z direction, the confocal signal continues to exhibit periodic sharp peaks when the laser beam focus crosses the optical interface 42, but the peak values are higher due to the increased reflectivity at the optical interface 42. Moreover, when the laser beam focus is scanned in the Z direction, it also crosses the second interface 43 between the air and the cornea. This second interface 43 can also reflect the laser beam and result in additional sharp peaks in the confocal signal.

Figure 6A:
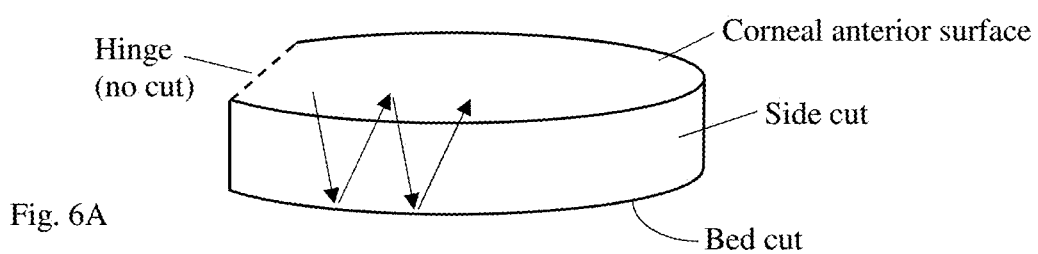
FIGS. 6A and 6B schematically illustrates forming a corneal flap, a procedure for which embodiments of the present invention may be implemented.
Figure 6B:
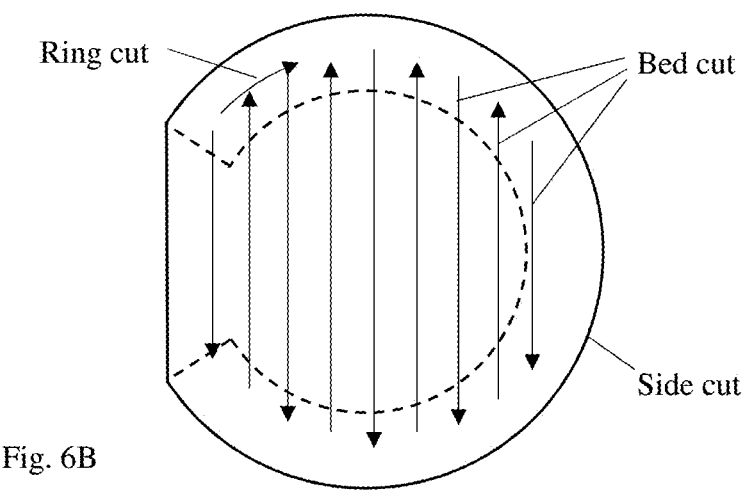
Figure 7A:
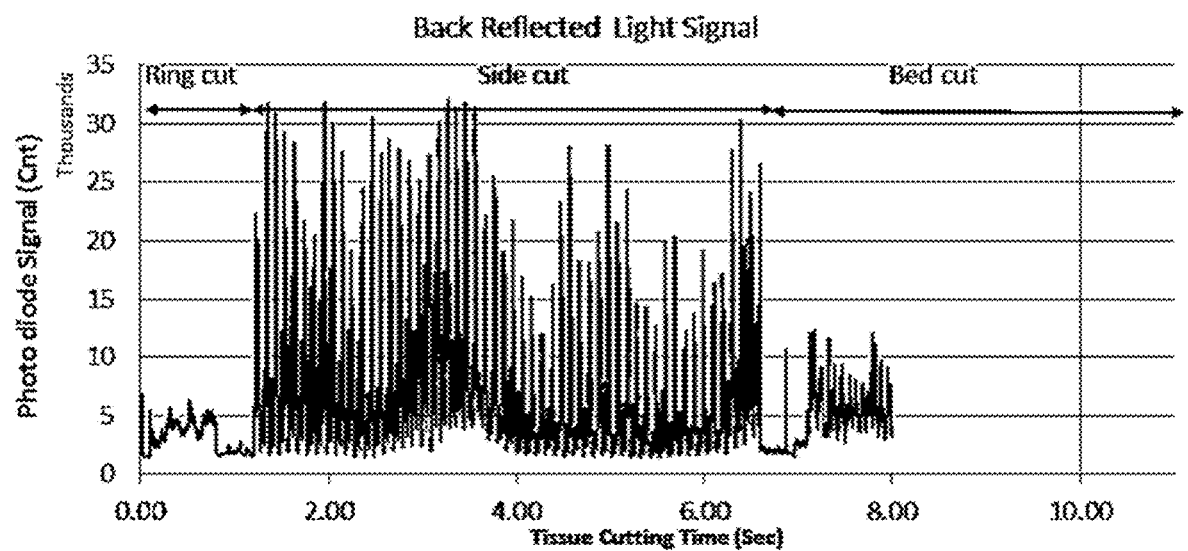
FIGS. 7A and 7B shows confocal signals from in experiments conducted when forming a corneal flap, when tissue contact was not lost and was lost during the cut, respectively.
Figure 7B:
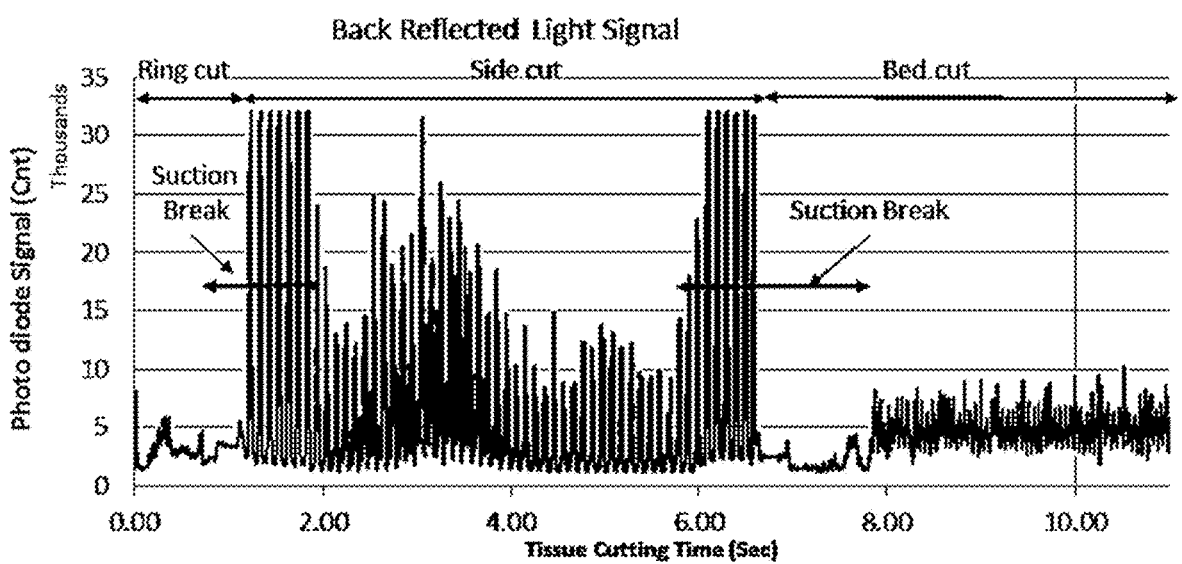

FIGS. 7A and 7B shows confocal signals in experiments conducted while performing incisions for a corneal flap. As schematically illustrated in FIGS. 6A and 6B, a corneal flap is formed by a bed cut which is parallel to the anterior corneal surface, and a side cut which is perpendicular or near perpendicular to the anterior corneal surface and which extends between the anterior corneal surface and the bed cut. In the top view, the side cut forms an incomplete circle surrounding the bed incision, with an uncut portion which forms a hinge of the flap. As shown in FIG. 6A, the side cut is performed by placing the fast scan line tangentially along the circle, moving the fast scan line in the Z direction back and forth between the depth of the bed cut and a position above the PI output surface, while also moving the fast scan line in the X-Y direction along the circle, forming a wave pattern along the side surface. In the example shown in FIG. 6B, the bed cut is formed by two scan patterns, referred to as a ring cut pattern and a bed cut pattern, both located in an X-Y plane. The ring cut pattern covers a peripheral area and the bed cut pattern covers a central area of the bed.

Docked porcine eyes were used in these experiments. During one procedure, a suction break in the PI suction channel was deliberately introduced using a wooden tip inserted between the porcine eye and the PI glass. The control procedure had no suction break. FIG. 7A shows the real-time confocal signal during the control procedure, including a first period when the laser beam focus is scanned in a ring cut pattern, a second period when the laser beam focus is scanned in a side cut patterns, and a third period when the laser beam focus is scanned in a bed cut pattern. FIG. 7B shows the real-time confocal signal from an experiment that included the same three scan periods, but suction breaks were created during two brief time intervals as indicated.

It can be seen from FIGS. 7A and 7B that the suction break during flap side cut caused the confocal signal peaks to increase to saturation when the laser beam focus traverses through the PI glass interface 41. This is analogous to the examples shown above in FIGS. 5A and 5B. During flap bed cut when the laser beam focus is inside the cornea and relatively far away from the PI glass interface, a suction break caused the confocal signal to be significantly reduced. This is analogous to the examples shown above in FIGS. 4A and 4B.

Another practical example of corneal procedure in which the confocal signal monitoring method may be implemented is the formation of a corneal inlay. A corneal inlay, which can be used to create a pocket in the cornea for an implant, includes a bed cut which is located inside the cornea and parallel to the anterior corneal surface, and an entry cut which extends between the anterior corneal surface and the bed but and reaches a peripheral portion of the bed cut. In the top view, the entry cut spans a small angular range of, for example, less than 30 degrees, and functions to provide access to the pocket. The behavior of the confocal signal during the bed cut and the entry cut are similar to those during the bed but and side cut in corneal flap formation described earlier.

Yet another practical example of ophthalmic procedure in which the confocal signal monitoring method may be implemented is the formation of a corneal lenticule. A more detailed description of corneal lenticule formation and extraction may be found in the above-referenced U.S. Pat. Appl. Pub. No. 2016/0089270. The corneal lenticule is formed by cutting a top lenticule cut and a bottom lenticule cut, each being a part of spherical shape or other curved or flat shapes. The top and bottom lenticule cuts may intersect each at their peripheries, or a side cut may be used to connect their peripheries, to form an isolated lenticule that can then be extracted from the cornea to effectuate refractive correction. One or more entry cuts are formed to provide assess for lenticule extraction, where the entry cuts extend between the anterior corneal surface and the peripheral edge of the top and/or bottom lenticule cuts. During the top and bottom lenticule cut and the side cut, the laser beam focus is entirely located inside the cornea. During the entry cut, the laser beam focus moves back and forth in the Z direction and crosses the PI lens surface multiple times. The behavior of the confocal signal during the top and bottom lenticule cuts and side cut, which are located insider the cornea, is similar to that during the bed cut in corneal flap formation; the behavior of the confocal signal during the entry cut is similar to that during the side cut in corneal flap formation, described earlier.

The confocal signal monitoring method may also be implemented in ophthalmic diagnostic procedures that require direct eye tissue contact, such as ultrasound pachymetry.

In embodiments of the present invention, the speed of confocal data acquisition is approximately 1 kHz or faster. As the controller 29 is electrically coupled to the both the scanning devices 21, 22, 25 and the confocal detection assembly 20, the controller can synchronize the output of the confocal detector with the laser beam focus position at a 1 kHz rate or greater. The controller can label each laser scan pattern, such as side cut, bed cut, etc., and apply corresponding analysis algorithms to the confocal signal. The behavior of the confocal signal associated with loss of tissue contact during different types of scans can be calibrated.

Figure 8:
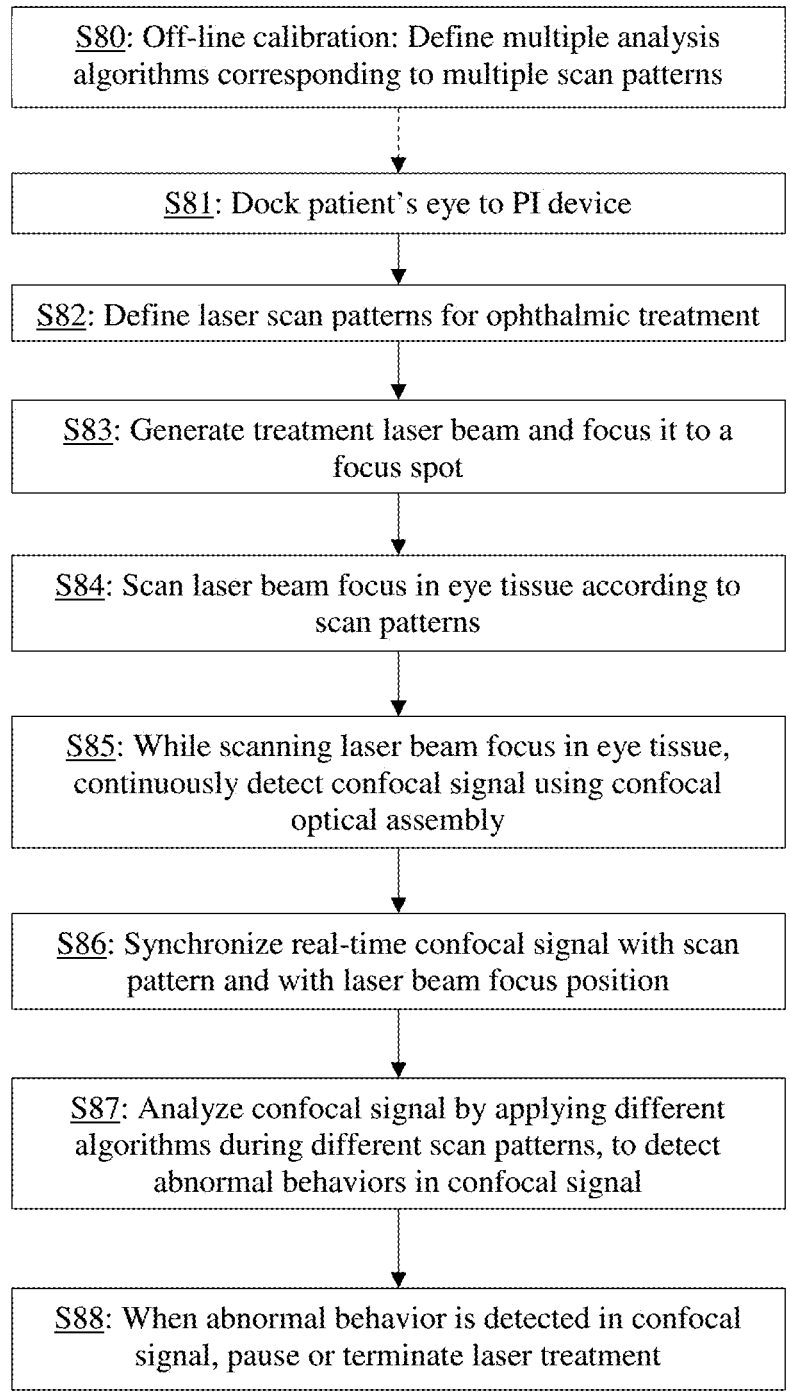
FIG. 8 schematically illustrates a method for detecting tissue contact lost based on confocal signals according to an embodiment of the present invention.

A method for detecting tissue contact loss during an ophthalmic laser procedure using confocal signal detection is described below with reference to FIG. 8.

First, the patient's eye is docked to the PI device such that the cornea is in contact with the PI output surface and the eye surface is securely attached to the PI device by the suction force in the PI's suction channel (step S81). An ophthalmic treatment procedure is defined, which includes various scan patterns for making various incisions or other tissue modifications (step S82). For example, the treatment procedure may be flap formation, and the various scan patterns may include a ring cut pattern, a bed cut pattern, a side pattern, etc. The treatment procedure is stored in the controller 29 of the laser system. A treatment laser beam is generated by the laser system and focused to a focus spot by the objective lens (step S83). The controller controls the scanning devices of the laser system (e.g. the fast-Z scanner 21, the resonant scanner 22, and/or the X-Y stages 25) to scan the laser beam focus in the eye tissue according to the scan patterns (step S84).

While the laser beam focus is being scanned according to the scan patterns, the confocal assembly continuously detects the confocal signal and outputs the detected signal to the controller in real time (step S85). The controller synchronizes the real-time confocal signal as a function of time with the laser beam focus position as a function of time (step S86). Here, the confocal signal is synchronized with at least the depth position of the laser beam focus, but may also be synchronized with the X-Y position as well. Note that when the laser beam scanning is faster than confocal signal acquisition (for example, the resonant scanner may have a scanning frequency of about 8 kHz while the confocal signal acquisition rate may be about 1 kHz), the laser beam focus position that is correlated with each confocal signal data point may be an average position. In step S86, the controller also synchronizes the real-time confocal signal with the scan patterns currently being performed, such as a ring cut pattern, a bed cut pattern, a side cut pattern, etc.

The controller analyzes, in real time, the confocal signal to detect abnormal behaviors in the signal (step S87). In this step, the controller applies different algorithms to analyze the confocal signal in different time periods, depending on the laser beam scan pattern currently being performed during each time period. As described earlier, the behavior of the confocal signal resulting from tissue contact loss is dependent on the current laser beam scan pattern. Thus, for example, during a bed cut for a corneal flap, the controller detects whether the confocal signal experiences a sudden drop in intensity that exceeds a predefined threshold; during a side cut, the controller detects whether the sharp peaks of the confocal signal, which are synchronized with the zero depth position during the side cut, experience a sudden increase in intensities that exceeds another predefined threshold.

In practice, the controller both controls the scanning devices based on predefined scan patterns and performs the confocal signal analyses; therefore, each time the controller changes the scan pattern to a new pattern, the controller can change the confocal signal analysis algorithm to a corresponding algorithm at the same time. This way, the confocal signal analysis algorithm is synchronized with the scan pattern.

When an abnormal behavior is detected in the confocal signal, the controller controls the laser system to pause or terminate laser treatment, generate a warning signal, and/or perform other suitable corrective actions (step S88).

Prior to treatment, an off-line calibration step (step S80) is performed to establish the various analysis algorithms, based on empirical studies of abnormal confocal signal behaviors corresponding to different scan patterns. This may be accomplished by performing different laser beam scan patterns in test samples, deliberately introducing suction breaks in the PI device during the scans, recording the corresponding confocal signals, and analyzing the confocal signal before and after suction breaks to design the analysis algorithms, including to determine the parameters such as the threshold values of intensity change. Some exemplary algorithms are given above; algorithms suitable for other types of scan patterns may be developed based on practical need.

To summarize, during an ophthalmic procedure, the confocal signal from the confocal detector can be used as an optical detector to monitor tissue contact with the PI output surface. Tissue contact to the PI output surface is also the ultimate goal of maintaining the eye suction and preventing relative eye movement. When the tissue contact is lost and detected by the confocal detector, it is an indication of suction loss or other eye fixation issues that require a treatment pause.

In addition to detection loss of tissue contact, the real time confocal signal may also be used during eye docking, where it functions as a cornea applanation state detector for providing docking endpoint feedback for assisted or automated docking control.

Figure 9:
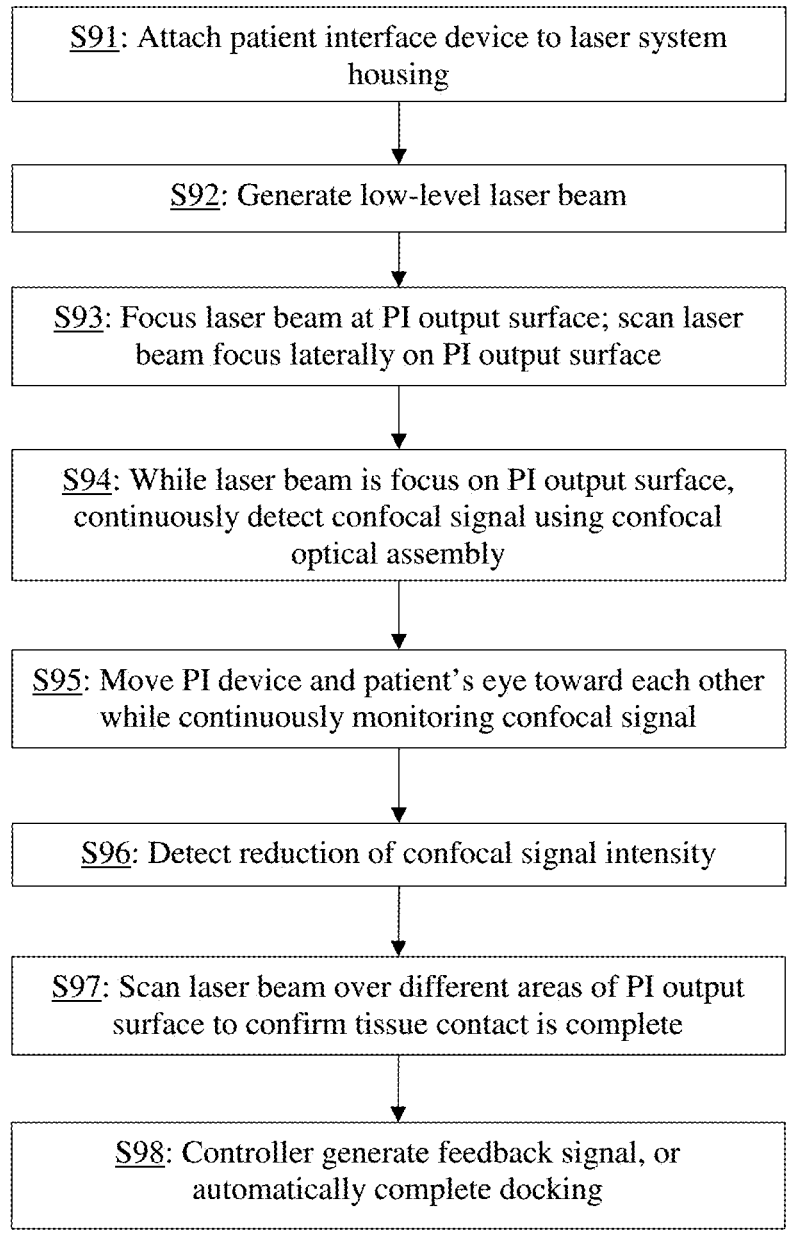
FIG. 9 schematically illustrates a method for assisted eye docking based on confocal signals according to another embodiment of the present invention.

An assisted docking process according to an embodiment of the present invention is described with reference to FIG. 9. The PI device is attached to the laser system housing prior to docking (step S91). A low-level laser light is generated by the laser system (step S92). For this purpose, the laser energy is reduced to an eye safe level that is well below treatment level. The laser beam is focused by the objective lens to a focus spot located at the PI output surface, and (optionally) the laser beam focus is scanned laterally on the PI output surface (step S93). The lateral scanning may be achieved using the X-Y stages alone, as high speed scanning is not essential. While the laser beam is focused at the PI output surface, the confocal assembly continuously detects the confocal signal and outputs the detected signal to the controller in real time (step S94).

While the confocal signal is continuously monitored by the controller, the PI device and the patient's eye are moved toward each other (step S95). This may involve moving the part of the laser system housing where the PI device is attached, or moving the patient, or both. When the eye tissue makes a direct contact with the PI output surface, the controller will detect a reduction of the confocal signal intensity that exceeds a predefined threshold, as the PI output surface changes from a lens-air interface to a lens-tissue interface with a lower reflectivity (step S96). After tissue contact is initially detected, the laser beam focus is scanned to different areas of the PI output surface to determine whether tissue contact has been established in an entire area of the PI output surface where tissue contact is required (step S97). The PI device and/or eye may be further moved until full contact is achieved and confirmed by the confocal signal.

The docking process may be performed manually, where the surgeon manually operates the laser system to move the PI device and the eye toward each other and manually determines when docking is complete. During such manual docking process, the controller generates a feedback signal for the surgeon based on the confocal signal, to indicate whether tissue contact is established and complete (step S98). Alternatively, the docking process (or the last stage thereof) may be performed automatically without the surgeon's intervention, where the controller controls the laser system to move the PI device and the eye toward each other, and uses the confocal signal to determine when tissue contact is established and complete, and automatically completes docking (step S98).

It will be apparent to those skilled in the art that various modification and variations can be made in the confocal signal-based eye suction loss and corneal applanation detection method of the present invention without departing from the spirit or scope of the invention. Thus, it is intended that the present invention cover modifications and variations that come within the scope of the appended claims and their equivalents.

What is claimed is:

1. An ophthalmic laser surgical method for treating an eye of a patient, comprising:
   coupling the eye to a patient interface device, including forming a direct contact of an output surface of the patient interface device with an eye tissue of the eye;
   a laser system generating a laser beam and focusing it to a laser beam focus;
   scanning devices of the laser system, controlled by a controller, scanning the laser beam focus within the eye according to one or more scan patterns;
   while the laser beam focus is being scanned within the eye, a confocal assembly of the laser system continuously detecting a confocal signal, the confocal signal representing an intensity of a portion of the laser beam that has been reflected by the eye, focused by one or more lenses onto a pinhole, passed through the pinhole, and detected by a photodetector behind the pinhole;
   based on the confocal signal, the controller detecting, in real time, a loss of the direct contact between the output surface of the patient interface device and the eye tissue; and
   in response to detecting the loss of the direct contact, the controller performing a predefined corrective action.

2. The method of claim 1, wherein scanning the laser beam focus within the eye modifies the eye.

3. The method of claim 2, wherein the one or more scan patterns include: a bed cut pattern and a side cut pattern in a cornea of the eye which collectively form a corneal flap, or a bed cut pattern and an entry cut pattern in the cornea which collectively form a corneal inlay, or two lenticule cut patterns and one or more entry cut patterns in the cornea which collectively form a corneal lenticule.

4. The method of claim 1, wherein the one or more scan patterns includes multiple scan patterns, and wherein the step of the controller detecting a loss of the direct contact includes applying different analysis algorithms to the confocal signal during different time periods when different scan patterns are used to scan the laser beam focus.

5. The method of claim 4, wherein the multiple scan patterns include a first scan pattern in which the laser beam focus is scanned within the eye at depths that are maintained below the output surface of the patient interface device, and
   wherein a first analysis algorithm is applied to the confocal signal while the first scan pattern is used to scan the laser beam focus, wherein the first analysis algorithm includes detecting a reduction in intensities of the confocal signal that exceeds a first predefined threshold, which indicates a loss of direct contact between the output surface of the patient interface device and the eye tissue.

6. The method of claim 5, wherein the multiple scan patterns further include a second scan pattern in which the laser beam focus is scanned with the eye at varying depths and the laser beam focus crosses the output surface of the patient interface device multiple times, and
   wherein a second analysis algorithm is applied to the confocal signal while the second scan pattern is used to scan the laser beam focus, wherein the second analysis algorithm includes detecting peaks of the confocal signal that correspond to the laser beam focus crossing the output surface of the patient interface device, and detecting an increase in peak intensities that exceeds a second predefined threshold.

7. The method of claim 4, wherein the controller controls the scanning devices to change from one scan pattern to another scan pattern at a defined time, and the controller changes the applied analysis algorithm from one algorithm corresponding to the one scan pattern to another algorithm corresponding to the other scan pattern at the defined time.

8. A method for docking an eye of a patient to a laser system, comprising:
coupling a patient interface device to a housing of the laser system;
the laser system generating a laser beam having an eye safe energy level and focusing it to a laser beam focus located at an output surface of the patient interface device;
while the laser beam focus is being focused at the output surface of the patient interface device, a confocal assembly of the laser system continuously detecting a confocal signal, the confocal signal representing an intensity of a portion of the laser beam that has been reflected by the output surface, focused by one or more lenses onto a pinhole, passed through the pinhole, and detected by a photodetector behind the pinhole;
a controller continuously monitoring the confocal signal;
while the confocal signal is being continuously generated and monitored, moving the patient interface device and the patient's eye toward each other;
based on the confocal signal, the controller detecting, in real time, formation of a direct contact between the output surface of the patient interface device and the eye; and
in response to detecting the formation of the direct contact, the controller performing a predefined responsive action.

9. The method of claim 8, wherein the step of detecting the formation of the direct contact includes detecting a reduction of an intensity of the confocal signal that exceeds a third predefined threshold.

10. The method of claim 9, further comprising:
in response to detecting the reduction of the intensity of the confocal signal, the controller controlling a scanning device of the laser system to move the laser beam focus laterally on the output surface of the patient interface device, and continuously monitoring the confocal signal to determine whether direct contact has been formed between a predefined area of the output surface of the patient interface device and the eye.

11. The method of claim 8, wherein the step of moving the patient interface device and the patient's eye toward each other is controlled automatically by the controller, and wherein the responsive action performed by the controller includes automatically stopping moving the patient interface device and the patient's eye toward each other.

12. The method of claim 8, wherein the responsive action performed by the controller includes generating a feedback signal indicating that the direct contact has been formed.

13. An ophthalmic laser surgical system, comprising:
a patient interface device having an output surface, the patient interface device configured to be coupled to a patient's eye to form a direct contact of the output surface with an eye tissue of the eye;
a laser device configured to generate a laser beam;
a focusing lens configured to focus the laser beam to a laser beam focus;
scanning devices configured to scan the laser beam focus;
a confocal assembly, including a beam splitter configured to sample a reflected portion of the laser beam that has been reflected by the eye or the output surface of the patient interface or both, a pinhole, a lens configured to focus the sampled reflected laser beam to the pinhole, and a detector located behind the pinhole configured to detect an intensity of the laser beam that has passed through the pinhole as a confocal signal;
a controller coupled to the scanning device and the confocal assembly, configured to:
control the scanning devices to scan the laser beam focus according to one or more scan patterns;
continuously receive the confocal signal generated by the confocal assembly;
based on the confocal signal, detect, in real time, a change in a state of direct contact between the output surface of the patient interface device and the eye tissue, including a change from a presence of direct contact to an absence of a direct contact, and a change from an absence of a direct contact to a presence of a direct contact; and
in response to detecting the change of the state of direct contact, perform a predefined responsive action.

14. The ophthalmic laser surgical system of claim 13, wherein the controller controls the scanning device to scan the laser beam focus within the eye to modify the eye, wherein the change is a loss of direct contact between the output surface of the patient interface device and the eye tissue.

15. The ophthalmic laser surgical system of claim 14, wherein the one or more scan patterns include multiple scan patterns, and wherein the controller detects the change by applying different analysis algorithms to the confocal signal during different time periods when different scan patterns are used to scan the laser beam focus.

16. The ophthalmic laser surgical system of claim 15, wherein the multiple scan patterns include a first scan pattern in which the laser beam focus is scanned within the eye at depths that are maintained below the output surface of the patient interface device, wherein a first analysis algorithm is applied to the confocal signal while the first scan pattern is used to scan the laser beam focus, wherein the first analysis algorithm includes detecting a reduction in intensities of the confocal signal that exceeds a first predefined threshold, which indicates a change from the presence to the absence of direct contact between the output surface of the patient interface device and the eye tissue,
wherein the multiple scan patterns further include a second scan pattern in which the laser beam focus is scanned with the eye at varying depths and the laser beam focus crosses the output surface of the patient interface device multiple times, and wherein a second analysis algorithm is applied to the confocal signal while the second scan pattern is used to scan the laser beam focus, wherein the second analysis algorithm includes detecting peaks of the confocal signal that correspond to the laser beam focus crossing the output surface of the patient interface device, and detecting an increase in peak intensities that exceeds a second predefined threshold, which indicates a change from the presence to the absence of direct contact between the output surface of the patient interface device and the eye tissue.

17. The ophthalmic laser surgical system of claim 15, wherein the controller controls the scanning devices to change from one scan pattern to another scan pattern at a defined time, and the controller changes the applied analysis algorithm from one algorithm corresponding to the one scan pattern to another algorithm corresponding to the other scan pattern at the defined time.

18. The ophthalmic laser surgical system of claim 13, wherein the laser beam has an eye safe energy level and is focused at the output surface of the patient interface device, wherein the change is a formation of direct contact between the output surface of the patient interface device and the eye, and wherein the controller detects the formation of the direct contact by detecting a reduction of an intensity of the confocal signal that exceeds a third predefined threshold.

19. The ophthalmic laser surgical system of claim 18, wherein the controller is further configured to:
   in response to detecting the reduction of the intensity of the confocal signal, control the scanning devices to move the laser beam focus laterally on the output surface of the patient interface device, and continuously monitor the confocal signal to determine whether direct contact has been formed between a predefined area of the output surface of the patient interface device and the eye.

20. The ophthalmic laser surgical system of claim 19, wherein the controller is further configured to control the laser device to move the patient interface device and the patient's eye toward each other while continuously receiving the confocal signal, and wherein the responsive action includes automatically controlling the laser device to stop moving the patient interface device and the patient's eye toward each other.

\* \* \* \* \*